United States Patent [19]

Ueno et al.

[11] 4,239,913

[45] Dec. 16, 1980

[54] PROCESS FOR PREPARING 2-HYDROXYNAPHTHALENECARBOXYLIC ACIDS

[75] Inventors: Ryuzo Ueno, Nishinomiya; Hiroaki Tsuchiya, Kobe; Yasukazu Muramoto, Itami; Yoshihiko Kuwae, Amagasaki, all of Japan

[73] Assignee: Kabushiki Kaisha Veno Seiyaku Oyo Kenkyujo, Osaka, Japan

[21] Appl. No.: 933,902

[22] Filed: Aug. 15, 1978

[30] Foreign Application Priority Data

Oct. 25, 1977 [JP] Japan .................... 52-127274
Oct. 26, 1977 [JP] Japan .................... 52-127642

[51] Int. Cl.³ .......................... C07C 51/15
[52] U.S. Cl. ................... 562/425; 562/423; 562/424
[58] Field of Search ............ 562/467, 423, 424, 425

[56] References Cited

U.S. PATENT DOCUMENTS

| 1,593,816 | 7/1926 | Andre | 260/520 A |
| 4,002,678 | 1/1977 | Quadbeck-Seeger et al. | 260/520 A |
| 4,020,102 | 4/1977 | Quadbeck-Seeger et al. | 260/520 A |
| 4,032,568 | 6/1977 | Quadbeck-Seeger | 260/520 A |
| 4,038,309 | 7/1977 | Hoch et al. | 260/520 A |

FOREIGN PATENT DOCUMENTS

| 2426850 | 1/1976 | Fed. Rep. of Germany . |
| 2426852 | 1/1976 | Fed. Rep. of Germany . |
| 2522175 | 11/1976 | Fed. Rep. of Germany . |
| 43/26612 | 1/1966 | Japan ................ 562/424 |
| 511393 | 8/1939 | United Kingdom ........ 562/467 |

OTHER PUBLICATIONS

BIOS Final Report No. 986, pp. 234–248.
Ullmanns Encyklopadie der Technischen Chemie, p. 606, 1960.

*Primary Examiner*—Paul J. Killos
*Attorney, Agent, or Firm*—Sherman & Shalloway

[57] ABSTRACT

A process for preparing 2-hydroxynaphthalenecarboxylic acids which comprises reacting a liquid mixture of 1 mole of an alkali β-naphtholate, 0.05 to 3 moles of β-naphthol, and 0.1 to 5 times the weight of the alkali β-naphtholate of light oil or kerosene with carbon dioxide under a carbon dioxide pressure of not more than 15 kg/cm².G at a temperature of at least 180° C.

13 Claims, 2 Drawing Figures

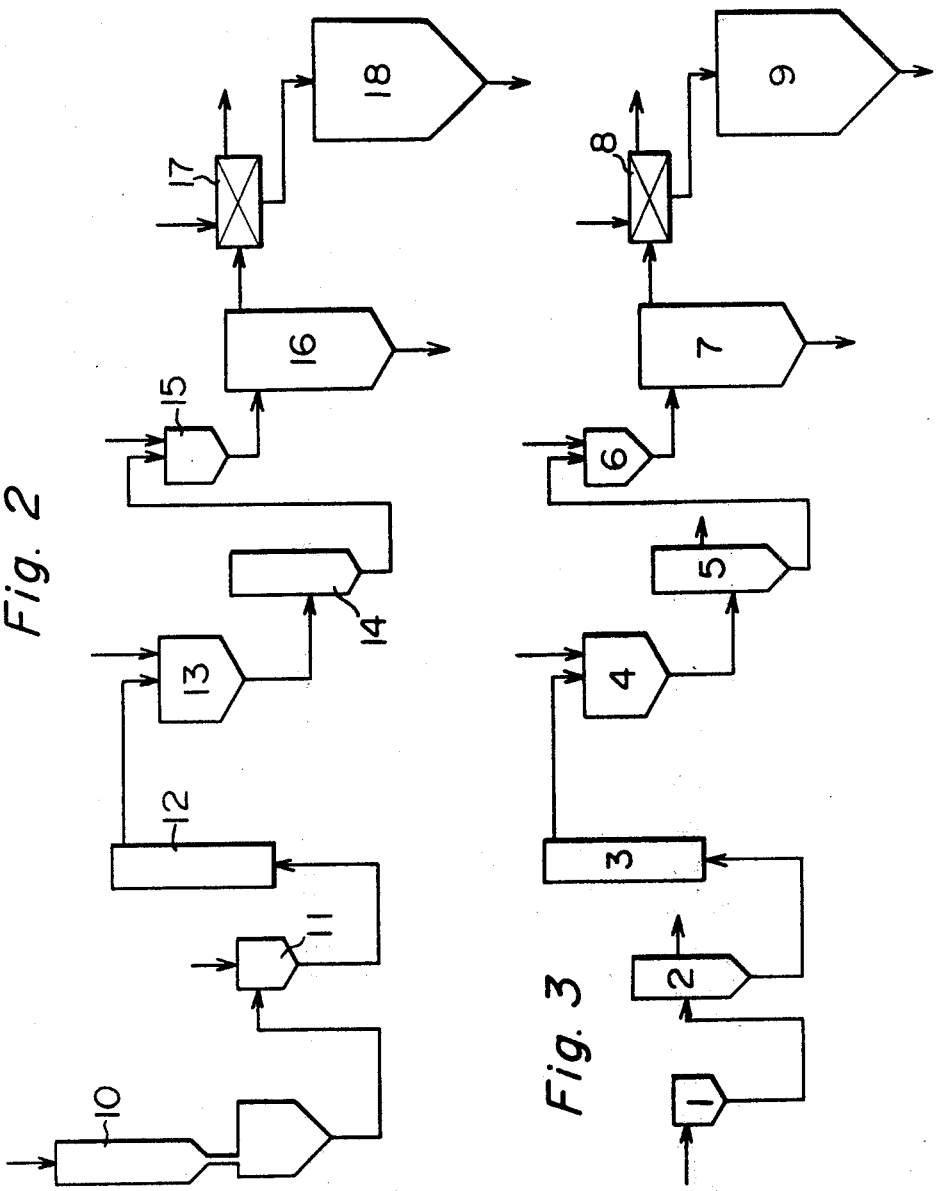

PROCESS FOR PREPARING 2-HYDROXYNAPHTHALENECARBOXYLIC ACIDS

This invention relates to a process for preparing 2-hydroxynaphthalenecarboxylic acids from alkali β-naphtholates.

Among 2-hydroxynaphthalenecarboxylic acids, 2-hydroxynaphthalene-3-carboxylic acids is especially important as an intermediate for pigments and dyes. Generally, it is prepared by reacting β-naphthol with an alkali hydroxide to form an alkali β-naphtholate, and reacting it with carbon dioxide under elevated pressure. It is important in this method to dry (i.e. dehydrate) the alkali β-naphtholate completely and effectively because the presence of even a small amount of water in this reaction decreases the yield of 2-hydroxynaphthalene-3-carboxylic acid. This conventional method requires a long period of more than 10 hours for the drying process and a complicated operation, and the cost of equipment and operation is high. In an attempt to overcome these difficulties, a method involving azeotropic dehydration of a solution of alkali β-naphtholate in diphenyl, diphenyl oxide, a mixture of these, or an alkylnaphthalene as a solvent was suggested. This method, however, has the disadvantage that the yield of the final product is not so high, and the solvents are expensive and malodorous and have too high a melting point or too low a boiling point.

A solid-gas phase reaction, known as the Kolbe-Schmidt reaction, has conventionally been used to react an alkali β-naphtholate with carbon dioxide. However, this method requires a long reaction time of, say, more than 50 hours because carboxylation and the recovery under reduced pressure of by-product β-naphthol must be repeatedly performed. Furthermore, losses of β-naphthol are great because of the thermal non-uniformity of the reaction at high temperatures. The reaction is difficult to control owing to changes in phase during the reaction, and stable yields are difficult to attain. To overcome these difficulties, a method which comprises carboxylating an alkali β-naphtholate in the presence of an excess of β-naphthol at a high pressure of 30 to 130 kg/cm$^2$.G, and a method which comprises carboxylating an alkali β-naphtholate in the presence of nitrilotriacetic acid or ethylenediamine-tetraacetic acid were suggested. These methods have neither proved entirely satisfactory because, for example, the yield of the desired product is low, the reaction must be carried out at high pressures, and an expensive material must be used to build the required reaction equipment.

On the other hand, there has been almost no report on the production of 2-hydroxynaphthalene-6-carboxylic acid in the literature.

In the process for producing 2-hydroxynaphthalene-3-carboxylic acid from sodium β-naphtholate in the optional presence of β-naphthol, it is economically important to recover β-naphthol formed as a by-product or added, and recycle the recovered β-naphthol either as such or as sodium β-naphtholate. Because 2-hydroxynaphthalene-3-carboxylic acid is a valuable starting material for the production of pigments and dyes and is required to have a very high purity, it is also important to separate β-naphthol and resinous matter from the final product.

One known method for separating β-naphthol and resinous matter from an aqueous solution containing a 2-hydroxynaphthalene-3-carboxylic acid salt comprises sedimenting a tarry layer containing β-naphthol and resinous matter from the aqueous solution, separating the sedimented tarry layer, cooling and filtering the aqueous upper layer to separate β-naphthol, and distilling the recovered mass under reduced pressure to recover β-naphthol. Another known method comprises adding water to the reaction mixture, extracting the resulting aqueous solution containing a 2-hydroxynaphthalene-3-carboxylic acid salt with benzene, an alkylbenzene or a halogenated benzene to obtain β-naphthol and resinous matter, and distilling the extract under reduced pressure to recover the extracting solvent and β-naphthol. In this method, the solvent used as a reaction medium in the reaction of alkali β-naphtholate with carbon dioxide is not used. A method is also known which comprises reacting alkali β-naphtholate with carbon dioxide using diphenyl, diphenyl ether, a mixture of these, or an alkyl naphthalene, adding water and sulfuric acid to the reaction mixture to liberate alkali β-naphtholate, separating the solvent layer, and extracting by counter-current extraction the aqueous layer containing the 2-hydroxynaphthalene-3-carboxylate with the same solvent to recover a β-naphthol-containing mixture. Because the resinous matter moves to the solvent layer in this method, all of the solvent layer and the β-naphthol-containing mixture must be distilled.

As is well known, a mixture of an alkali β-naphtholate and β-naphthol becomes liquid at a temperature at which a 2-hydroxynaphthalenecarboxylic acid is formed by reaction with carbon dioxide. The 2-hydroxynaphthalenecarboxylic acid salt as a final product precipitates as a solid out of the reaction system. The solid product that has precipitated envelops the liquid material, and consequently, the reaction system becomes a heterogeneous mass so that the reaction cannot be carried out smoothly. This is presumably the reason why the reaction requires a pressure of as high as at least 30 kg/cm$^2$.G and the yield decreases.

The present inventors made extensive investigations in order to secure good contact between an alkali β-naphtholate and carbon dioxide during their reaction in the liquid state, and to lower the melting point of the liquid mixture for convenience of transportation in a continuous operation. These investigations led to the discovery that when a liquid mixture composed of 1 mole of an alkali β-naphtholate, 0.05 to 3 moles of β-naphthol and light oil (i.e. gas oil) or kerosene is used and the weight of the light oil or kerosene is adjusted to 0.1 to 5 times that of the alkali β-naphtholate, distribution of β-naphthol to a layer of the alkali β-naphtholate/β-naphthol liquid mixture and to the light oil or kerosene layer is effected properly, and the specific gravities of the two layers approximate each other to form a good suspension; and consequently that the reaction can be performed continuously at an increased rate and with an increased output per unit reactor to afford pure 2-hydroxynaphalenecarboxylic acids with a reduced tar content in high yields. The term "light oil (or gas oil) or kerosene", as used herein, denotes petroleum hydrocarbons having a boiling point of about 150° to 400° C., preferably 180° to 350° C.

Furthermore, the present inventors continued their work on the dehydration of the alkali β-naphtholate and the alkali β-naphtholate in the alkali β-naphtholate/β-naphthol mixture. Consequently, they found that these alkali β-naphtholates can be well dispersed in the light oil or kerosene, and dehydration of the alkali β-naphtholate in this medium can be performed with good efficiency within short periods of time.

Thus, dehydration of the alkali β-naphtholate and the reaction of the dehydrated alkali β-naphtholate with carbon dioxide can be carried out continuously in the light oil or kerosene. When the alkali β-naphtholate is carried out in light oil or kerosene, the amount of the light oil or kerosene is preferably large (for example, about 2 to 7 times the weight of the alkali β-naphtholate) to increase the efficiency of dehydration and transportation. When the light oil or kerosene is used for dehydration in an amount exceeding 5 times the weight of the alkali β-naphtholate, the excess of the light oil or kerosene must be separated from the liquid mixture of the alkali β-naphtholate, β-naphthol and the light oil or kerosene prior to reaction with carbon dioxide. This separation can be performed simply by a liquid separating technique.

The present inventors also worked on a method which can recover 2-hydroxynaphthalene-3-carboxylic acid in high purity from the reaction mixture, recovering β-naphthol and separating the resinous matter. They found that when water is added to the reaction mixture to separate the light oil or kerosene layer and then an acid is added to the aqueous layer to liberate β-naphthol, the tarry layer containing β-naphthol and the resinous matter sediments as a liquid, and at this time, β-naphthol forms a eutectic mixture containing about 13% of water and a small amount of the resinous matter which has a melting point of about 90° C. Alternatively, a tarry layer containing β-naphthol and resinous matter can be sedimented as a liquid from the aqueous layer by adding an acid to the reaction mixture to liberate β-naphthol and then separating the light oil or kerosene layer. In either case, the light oil or kerosene layer does not substantially contain the resinous matter.

On the basis of the above findings, the present invention provides a process for preparing 2-hydroxynaphthalene carboxylic acids, which comprises reacting a liquid mixture consisting of 1 mole of an alkali β-naphtholate, 0.05 to 3 moles of β-naphthol and 0.1 to 5 times the weight of the alkali p-naphtholate of light oil or kerosene with carbon dioxide at a temperature of at least 180° C. under a pressure of not more than 15 kg/cm$^2$.G.

In a preferred embodiment of the invention, the alkali β-naphtholate or the mixture of alkali β-naphtholate and β-naphthol is dehydrated in light oil or kerosene, and the resulting liquid mixture is reacted with carbon dioxide under the above-mentioned conditions.

The desired product is separated from the reaction mixture preferably by adding water to the reaction mixture, separating the light oil or kerosene layer before or after liberating the unreacted alkali β-naphtholate as β-naphthol with an acid, if required adding an acid to the aqueous layer, sedimenting and separating a tarry layer containing β-naphthol and resinous matter as a liquid from the aqueous layer, extracting β-naphthol from the aqueous layer by using a hydrophobic extracting solvent, and precipitating the desired product with an acid from the aqueous layer after the extraction. It is especially advantageous in this case to recover from the light oil or kerosene layer and/or the tarry layer and/or the solvent extract layer β-naphthol either as such or as an alkali β-naphtholate by using an alkali hydroxide.

According to this invention, the reaction of the alkali β-naphtholate or β-naphthol with carbon dioxide, the dehydration of the starting materials, the work-up of the reaction mixture can be performed either by a batchwise process or by a continuous process. It is especially preferred however to combine these steps and perform them continuously. In the continuous process, the starting materials are dehydrated as stated hereinabove and reacted under the aforesaid conditions. Then, β-naphthol recovered from the reaction mixture as such and/or as alkali β-naphtholate is recycled to the dehydrating step.

In the practice of the process of the invention, a liquid mixture consisting of 1 mole of an alkali β-naphtholate, 0.1 to 3 moles, especially 0.2 to 2 moles, of β-naphthol, and 0.1 to 5 times, preferably 0.2 to 4 times, especially preferably 0.5 to 3 times, the weight of the alkali β-naphtholate of light oil or kerosene (a petroleum hydrocarbon having a boiling point of 150° to 400° C., preferably 180° to 350° C.) is reacted with carbon dioxide at a temperature of at least 180° C., especially 250° to 280° C., under a carbon dioxide pressure of not more than 15 kg/cm$^2$.G, preferably 1 to 10 kg/cm$^2$.G, especially preferably 2 to 7 kg/cm$^2$.G. When the amount of the light oil or kerosene exceeds the upper limit specified above, the yield of the product decreases. For example, when the light oil or kerosene is used in an amount 6 times as large as the weight of the alkali β-naphtholate, the yield of the product based on the alkali β-naphtholate is less than 10%. The reaction time is generally 2 to 5 hours. The starting liquid mixture described above is prepared in a customary manner.

According to a preferred embodiment of this invention, an alkali β-naphtholate or a mixture of it with β-naphthol is dehydrated in light oil or kerosene, and then the starting liquid mixture of the aforesaid composition is prepared. The alkali β-naphtholate is dehydrated by a procedure which involves reacting β-naphthol and an aqueous solution of an alkali hydroxide in light oil or kerosene, or adding an aqueous solution of alkali β-naphtholate to the aforesaid medium and stirring the mixture, thereby to suspend the hydrous alkali β-naphtholate in the medium; and then heating the suspension in an inert gas such as nitrogen. This procedure may be performed in combination with, for example, a method involving dehydrating a mixture of the hydrous alkali β-naphtholate and light oil or kerosene by a piston flow. When the mixture of alkali β-naphtholate and β-naphthol is to be subjected to a dehydration treatment, β-napthol is reacted with an aqueous solution of an equivalent or lesser amount of an alkali hydroxide in light oil or kerosene, or a hydrous mixture of alkali β-naphtholate and β-naphthol is suspended in the medium, followed by the same dehydrating method as described above. Or this can be performed by adding a desired amount of β-naphthol at an optional stage in the above-described dehydration method. In these dehydrating procedures, a suitable dehydration agent can be used.

After the dehydration, β-naphthol is added as required to prepare a liquid mixture of the aforesaid composition. The mixture is then reacted with carbon dioxide under the aforesaid conditions. When the alkali β-naphtholate is dehydrated in light oil or kerosene, the excess of light oil or kerosene is removed by a liquid separating technique from the resulting liquid mixture of the alkali β-naphtholate, β-naphthol and light oil or kerosene and then if desired, β-naphthol is further added to prepare a liquid mixture of the aforesaid composition.

The work-up of the reaction mixture can be performed in a customary manner. In a preferred embodiment of this invention, the work-up is performed, for example, as follows: After the reaction, the reaction mixture is cooled, and water is added. When a 2-hydroxynaphthalene-1-carboxylic acid salt is present, the mixture is heated to decompose it to β-naphthol. The mixture is then separated into a light oil or kerosene layer and an aqueous layer and the light oil or kerosene layer is separated. An acid, such as a mineral acid or an aqueous solution of a mineral acid, is added to the aqueous layer to adjust the pH preferably to 4 to 8, especially 5 to 7, to liberate the unreacted alkali β-naphtholate as β-naphthol. A tarry layer containing β-naphthol and resinous matter is sedimented as a liquid at 80° to 100° C. The tarry layer separated is preferably washed with water, and the washing is reused as a portion of the water to be added. It is also possible at this time to add water to the reaction mixture, adjust the pH to the desired value by an acid, then separate the mixture into a light oil or kerosene layer and an aqueous layer, and separate the sedimented tarry layer from the aqueous layer. After the separation of the tarry layer, β-naphthol is extracted from the aqueous layer by using a hydrophobic extracting solvent.

Useful extracting solvents include hydrocarbons such as benzene, toluene, xylene, hexane and cyclohexane; halogenated hydrocarbons such as chlorobenzene, dichloromethane, dichloroethane and chloroform; nitrated hydrocarbons such as nitrobenzene and nitromethane; ethers such as dibutyl ether and diphenyl ether; ketones such as cyclohexanone, diisobutyl ketone and acetone; alcohols containing at least 4 carbon atoms such as n-butyl alcohol, n-octyl alcohol and 2-ethylhexyl alcohol; and mixtures of these solvents. Preferably, the extracting solvent is used in an amount corresponding to 0.3 to 2 times, especially 0.5 to 1.5 times, the volume of the aqueous layer, and the extraction is carried out preferably at 30° to 110° C., especially at 50° to 100° C.

β-Naphthol in the reaction medium layer and in the extract solvent layer can be recovered in a customary manner, for example by distillation under reduced pressure. Preferably, it is recovered as an alkali β-naphtholate solution by using an alkali hydroxide solution. β-Naphthol in the tarry layer is recovered by vacuum distillation, etc. The recovered aqueous solution of alkali β-naphtholate is recycled to the aforesaid dehydrating step, and β-naphthol, to the dehydrating step and/or the reaction step. The aforesaid extraction results in the removal of tiny amounts of the reaction medium in the aqueous layer, and the inclusion of resinous matter into the extracted layer does not substantially occur. By adjusting the pH of the aqueous layer left after the extraction by using an acid, preferably an aqueous solution of a mineral acid, the desired product can be precipitated and separated.

The process of this invention can be performed continuously, and usually after a reaction period of 2 to 5 hours, the yield of the product based on alkali β-naphtholate reaches about 45%, and the yield based on the consumed β-naphthol exceeds 85%. The ratio of recovery of β-naphthol reaches about 95%. The light oil or kerosene used as the reaction medium is available at low prices, and has good properties. Furthermore, good results can be obtained even when the pressure of carbon dioxide is about 3 to 5 kg/cm$^2$.G. The reaction apparatus can be made of an inexpensive material.

It is not necessary to distill off β-naphthol during reaction, and it can be recovered and recycled. The alkali β-naphtholate or the mixture of it with β-naphthol can be dehydrated within a period of as short as a few hours, and this step can be continuously performed. β-Naphthol can be recovered as an aqueous solution of alkali β-naphtholate from the reaction mixture and the extracting solvent, and recycled. It is also possible to adjust the proportion of alkali β-naphtholate recycled to a suitable one for the balance of the recycle substance, for example to make it a major proportion of the entire β-naphthol. Or it is possible to make the amount of β-naphthol recovered from the tarry layer nearly equal to the amount of β-naphthol added to the reaction system. The yield of the product based on the consumed β-naphthol and the ratio of recovery of β-naphthol are high as stated above, and the loss of β-naphthol is extremely low.

In contrast to the known methods which require vacuum distillation of the entire β-naphthol-containing mixture recovered including the solvent, the process of this invention is very advantageous both operationally and economically. The reaction medium and the extraction solvent can be recycled without the need for heating or cooling procedures such as fractional distillation, the process is very advantageous from the viewpoint of thermal economy. These solvents are hardly lost by deterioration or other cause, and the ratio of recovery of the reaction medium and extraction solvent is more than 99.5%.

The 2-hydroxynaphthalenecarboxylic acid obtained by the process of the invention has a purity of more than 99%, and the proportion of β-naphthol contained as an impurity is less than 0.1%. The process of this invention is advantageous from the viewpoint of thermal economy because the separation of the reaction medium layer, the separation of the tarry layer, the extraction of the aqueous layer and acid precipitation of the product after the reaction can be performed at nearly the same temperature. The process of the invention has also made possible the continuous practice of all of the steps of forming 2-hydroxynaphthalenecarboxylic acid from β-naphthol, and is very useful for commercial operation.

The following non-limiting Examples and the accompanying drawings are given to illustrate the present invention more specifically.

In the accompanying drawings,

FIG. 2 is a diagram of the apparatus used in Examples 4 and 6; and

FIG. 3 is the diagram of the apparatus used in Examples 7, 8 and 9.

EXAMPLE 1

Figure 1:
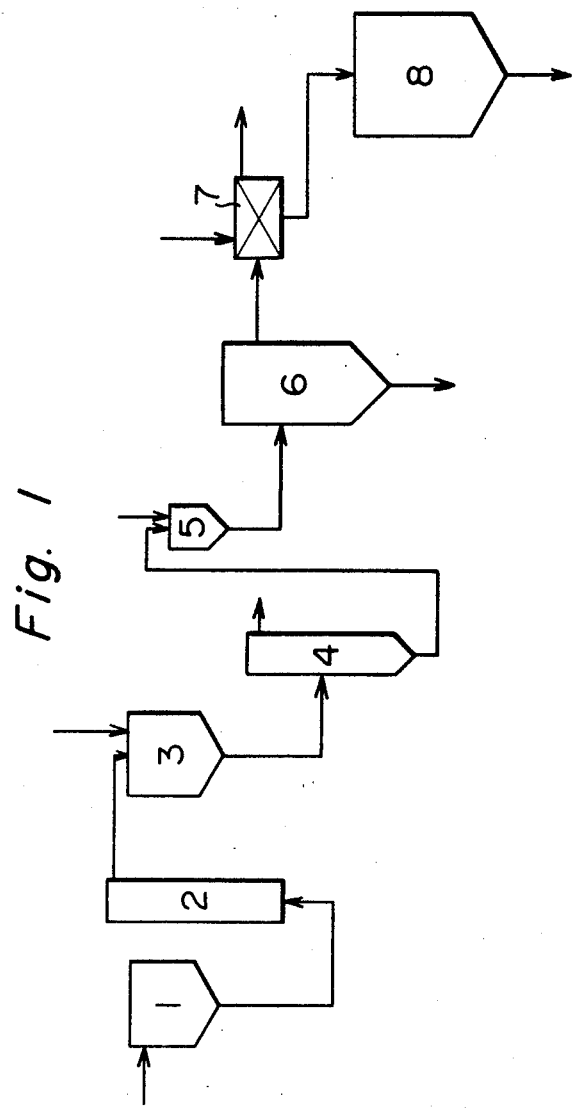
FIG. 1 is a diagram of the apparatus used in Example 3.

An autoclave was charged with 434 g of light oil (boiling at 200°–310° C.) and 166 g of sodium β-naphtholate, and with stirring, 144 g of β-naphthol was added. The mixture was reacted with carbon dioxide under a pressure of 3 kg/cm$^2$.G at a temperature of 260° C. for 3 hours.

The reaction mixture was added to 830 ml of water, and heated at 100° C. for 30 minutes to decompose a 2-hydroxynaphthalene-1-carboxylic acid salt. Then, the mixture was separated at 85° C. into a light oil layer and an aqueous layer. The pH of the aqueous layer was adjusted to 5.5 with hydrochloric acid, and at the same temperature as above, the tarry layer that sedimented was separated. The aqueous layer was extracted with 500 ml of toluene at 80° C. The pH of the aqueous layer was adjusted to 2.0 with hydrochloric acid at 85° C. The aqueous layer was then cooled to 40° C. and filtered to afford 81.2 g of 2-hydroxynaphthalene-3-carboxylic acid (melting range 220° to 221° C.; purity 99.4%; β-naphthol content 0.06%).

The yield of the product based on sodium β-naphtholate was 43.2%. 214.8 g of β-naphthol was recovered. The yield of the product based on the β-naphthol consumed was 85.0% and the ratio of recovery of β-naphthol was 95.2%.

EXAMPLE 2

By using 830 g of kerosene (boiling at 180°–260° C.) instead of the light oil in Example 1, the reaction was performed at a carbon dioxide pressure of 5 kg/cm$^2$. G at a reaction temperature of 250° C. for 5 hours.

The reaction mixture was worked up in the same way as in Example 1 except that 500 ml of methyl isobutyl ketone was used instead of toluene. Thus, 76.1 g of 2-hydroxynaphthalene-3-carboxylic acid (melting range 219°–221° C.; purity 99.4%; β-naphthol content 0.05%) was obtained.

The yield of the product based on sodium β-naphtholate was 40.5%. 219.5 g of β-naphthol was recovered, and the yield of the product based on the β-naphthol consumed was 85.1%. The ratio of recovery of β-naphthol was 95.5%.

EXAMPLE 3

By using the apparatus shown in FIG. 1, the reaction and after-treatment was continuously carried out.

A mixer 1 was fed hourly with 83 kg of sodium β-naphtholate, 130 g of light oil (boiling at 200°–310° C.) and 72 kg of β-naphthol, and they were dispersed and mixed. The dispersion was fed into a reactor 2 maintained at a carbon dioxide pressure of 3 kg/cm$^2$.G at a rate of 285 kg/hr, and reacted at 270° C. The residence time was 4.5 hours. The reaction mixture which left the reactor 2 was cooled in a heat exchanger (not shown), and mixed with 420 liters/hr of water in the stirring tank 3. The temperature of the mixture was adjusted to 85° C., and the mixture was then fed into a separating tank 4 where it was separated at 85° C. into a light oil layer and an aqueous layer. The upper light oil layer was passed through a recovery device (not shown) to recover β-naphthol. The pH of the lower aqueous layer was adjusted to 5.5 with dilute sulfuric acid in a pH adjusting tank 5, and it was separated at 85° C. in a separating tank 6. By using a vacuum distillation device (not shown), β-naphthol was recovered from the separated lower tarry layer. The upper layer in the separating tank 6 was sent to a centrifugal extracting device 7 where it was extracted at 85° C. with 250 liters/hr of xylene. The xylene layer was sent to a recovery device (not shown) to recover β-naphthol. The aqueous layer in the extracting tank 7 was sent to an acid precipitation tank 8, and its pH was adjusted to 2.0 with dilute sulfuric acid at 85° C., followed by acid precipitation. Thus, 42.3 kg/hr of 2-hydroxynaphthalene-3-carboxylic acid (melting range 220°–221° C.; purity 99.5% β-naphthol content 0.03%) was obtained.

The yield of the product based on sodium β-naphtholate was 45.0%. β-Naphthol was recovered at a rate of 106.0 kg/hr. The yield of the product based on the β-naphthol consumed was 85.2%, and the ratio of recovery of β-naphthol was 95.0%.

EXAMPLE 4

The operation was continuously performed by using the apparatus shown in FIG. 2.

A mixture consisting of 97.7 kg of an 85% aqueous solution of sodium β-naphtholate and 193 kg of light oil was fed into an evaporator 10 at a rate of 290.7 kg per hour, and dehydrated at 250° C. with a residence time of 3 hours. The resulting mixture consisting of 83 kg of sodium β-naphtholate and 166 kg of light oil (boiling at 200°–310° C.) was fed into a mixer 11 at a rate of 249 kg/hr. In the mixer, β-naphthol was added in an amount of 36 kg per hours and dispersed. The resulting dispersion was sent at a rate of 285 kg/hr to a reactor 12 maintained at a carbon dioxide pressure of 3 kg/cm$^3$.G, and reacted at 270° C. with a residence time of 4.5 hours. The reaction mixture which left the reactor 12 was cooled in a heat exchanger (not shown), and then mixed with 500 liters/hr of water in a stirring tank 13. The mixture was separated into a light oil layer and an aqueous layer at 85° C. in a separating tank 14. β-Naphthol was recovered from the upper light oil layer by using a recovery device (not shown). The lower aqueous layer was sent to a pH adjusting tank 15 where its pH was adjusted to 5.5 with hydrochloric acid. The mixture was then fed into a separating tank 16. From the lower tarry layer in the separating tank 16, β-naphthol was recovered by using a vacuum distillation device (not shown). The upper layer was extracted with 250 liters/hr of xylene in an extracting device 17 at 85° C. The xylene layer was sent to a recovery device (not shown) to recover β-naphthol. The aqueous layer in the extracting tank 17 was sent to an acid precipitating tank 18, and its pH was adjusted to 2.0 with hydrochloric acid at 85° C. Thus, 2-hydroxynaphthalene-3-carboxylic acid (melting range 220°–221° C.; purity 99.5%; β-naphthol content 0.03%) was obtained at a rate of 39.8 kg/hour.

The yield of the product based on sodium β-naphtholate was 42.3%, and the amount of β-naphthol recovered was 72.2 kg. The yield of the product based on the β-naphthol consumed was 85.0%, and the ratio of recovery of β-naphthol was 93.1%.

EXAMPLE 5

An autoclave was charged with 498 g of light oil (boiling at 250°–350° C.) and 166 g of sodium β-naphtholate, and with stirring, 72 g of β-naphthol was added. The mixture was reacted with carbon dioxide under a pressure of 5 kg/cm$^2$.G at a reaction temperature of 270° C. for 4 hours. The reaction mixture was added to 830 ml of water, and heated at 100° C. for 30 minutes to decompose a 2-hydroxynaphthalene-1-carboxylic acid salt. The mixture was then separated into a light oil layer and an aqueous layer at 85° C. From the light oil layer, β-naphthol was extracted as an aqueous solution of sodium β-naphtholate by using an aqueous solution of sodium hydroxide. The pH of the aqueous layer was adjusted to 5.5 with hydrochloric acid, and the tarry layer that sedimented was separated at 85° C., and β-naphthol was recovered from the tarry layer by vacuum distillation. Water (500 ml) was added to the aqueous layer, and the mixture was extracted with 650 ml of toluene at 80° C. From the toluene layer, β-napthol was extracted as an aqueous solution of sodium β-naphtholate by using an aqueous solution of sodium hydroxide. The pH of the aqueous layer was adjusted to 2.0 with hydrochloric acid, and the mixture was cooled to 40° C., followed by filtration. Thus, 79.9 g of 2-hydroxynaphthalene-3-carboxylic acid (melting range 220°–221° C.; purity 99.6%; β-naphthol content 0.03%) was obtained.

The yield of the product based on sodium β-naphtholate was 42.5%. Sodium β-naphtholate was recovered in a total amount of 61.5 g (53.3 g as β-napthol; 28.6 g from the light oil layer and 32.9 g from the toluene layer). From the tarry layer, 90.6 g of β-naphthol was recovered. The yield of the product based on the β-naphthol consumed was 85.1%, and the ratio of recovery of β-naphthol was 93.1%. Furthermore, 497 g of light oil and 648.7 ml of toluene were recovered. The amounts of these recovered corresponded each to a recovery ratio of 99.8%.

By using the recovered sodium β naphtholate, β-naphthol, light oil and toluene recyclically, the same reaction and the same separating and extracting steps as described above were carried out. There was hardly any change in the yield and purity of 2-hydroxynaphthalene-3-carboxylic acid and the recovery ratios of β-naphthol, light oil and toluene.

When monochlorobenzene or n-dibutyl ether was used as the extracting solvent, much the same results as above were obtained.

Furthermore, when in the above procedure, the pH of the mixture before the separation of it into a light oil layer and an aqueous layer was adjusted to 5.5 by using hydrochloric acid, much the same results were obtained.

EXAMPLE 6

Using the same apparatus as used in FIG. 2 but not containing mixer 11, the following operation was continuously carried out.

A mixture consisting of 97.7 kg of an 85% aqueous solution of sodium β-naphtholate, 45.4 kg of β-naphthol and 99.6 kg of light oil (boiling at 200°–310° C.) was fed into an evaporating device 10 at a rate of 242.7 kg per hour, and dehydrated at 250° C. for 1 hour. β-Naphthol which distilled out together with light oil was recovered by a separately provided device (not shown). A dispersion consisting of 83 kg of sodium β-naphtholate, 43.2 kg of β-naphthol and 83 kg of light oil was fed into a reactor 12 maintained at a carbon dioxide pressure of 3 kg/cm$^2$.G at a rate of 209.2 kg/hour, and reacted at 270° C. The residence time was 4.5 hours. The reaction mixture was worked up in the same way as in Example 4 to afford 42.5 kg/hour of 2-hydroxynaphthalene-3-carboxylic acid (melting range 220°–221° C.; purity 99.6%; β-naphthol content 0.02%).

The yield of the product was 45.2% based on sodium β-naphtholate and 86.6% based on the β-naphthol consumed. The amount of β-naphthol recovered was 77.6 kg per hour, and the ratio of recovery of β-naphthol was 93.9%.

EXAMPLE 7

The following operation was continuously performed by using the apparatus shown in FIG. 3.

A mixer 1 was fed hourly with 83 kg of sodium β-naptholate, 181 kg of light oil (boiling at 200°–310° C.) and 57.2 kg of β-naphthol, and they were mixed and dispersed. About one-third of the light oil layer (upper layer) formed in the separating tank was removed, and fed into a recovery apparatus (not shown) to recover the dissolved β-naphthol and a tiny amount of sodium β-naphtholate as an aqueous solution of sodium β-naphtholate. The mixture remaining in the separating tank 2 consisted of 81 kg of sodium β-naphtholate, 42.4 kg of β-naphthol and 130 kg of light oil. The liquid mixture was fed into a reactor 3 at a rate of 253.4 kg per hour, and reacted with carbon dioxide at a pressure of 5 kg/cm$^2$.G and a temperature of 250° C. The residence time was 5 hours. The reaction mixture which left the reaction tank 3 was cooled in a heat exchanger (not shown), and mixed with 400 liters/hour of water in a stirring tank 4, and sent to a separating tank 5 where the mixture was separated at 85° C. into a light oil layer and an aqueous layer. From the upper light oil layer, β-naphthol was recovered by using a recovery device (not shown). The lower aqueous layer was sent to a pH adjusting tank 6, and after adjusting its pH to 5.5 with dilute sulfuric acid, was introduced into a separating tank 7. From the lower tarry layer in the separating tank 7, β-naphthol was recovered by using a vacuum distillation device (not shown). The upper layer was sent to an extracting device 8 where it was extracted with 250 liters/hr of xylene at 80° C. The xylene layer was sent to a recovery device (not shown) to recover β-naphthol. The aqueous layer in the extracting tank 8 was sent to an acid precipitation tank 9 where it was subjected to acid precipitation at a pH of 2.0 using dilute sulfuric acid at 85° C. Thus, 41.3 kg/hr of 2-hydroxynaphthalene-3-carboxylic acid (melting range 220°–221° C.) was obtained.

The yield of the product was 45.0% based on the sodium β-naphtholate and 85.6% based on the β-naphthol consumed. The amount of β-naphthol was 75.6 kg per hour, and the ratio of recovery of β-naphthol was 93.4%.

EXAMPLE 8

In mixer 1 in FIG. 3, 83 kg of sodium β-naphtholate, 181 kg of kerosene and 57.2 kg of β-naphthol were mixed and dispersed hourly. About two-thirds of the kerosene layer formed in separating tank 2 was removed, and from it, β-naphthol and sodium β-naphtholate were recovered as an aqueous solution of sodium β-naphtholate. The liquid mixture consisting of 79 kg of sodium β-naphtholate, 27.6 kg of β-naphthol and 80 kg of kerosene remaining in the separating tank 2 was fed at a rate of 186.6 kg/hr into the reactor 3, and reacted with carbon dioxide under a pressure of 5 kg/cm$^2$.G with a residence time of 5 hours. The reaction mixture was worked up in the same way as in Example 7 except that hydrochloric acid was used for pH adjustment in the pH adjusting tank 6 and the acid precipitation tank 9, and toluene was used as the extracting solvent in the extracting tank. Thus, 40.3 kg/hr of 2-hydroxynaphthalene-3-carboxylic acid (melting range 218.5°–221° C.) was obtained.

The yield of the product was 45.0% based on sodium β-naphtholate and 85.9% based on the β-naphthol consumed. The amount of β-naphthol recovered was 60.4 kg/hour, and the ratio of recovery of β-naphthol was 92.3%.

EXAMPLE 9

A mixture consisting of 97.7 kg of an 85% aqueous solution of sodium β-naphthol and 208 kg of light oil (boiling at 250°–350° C.) was sent to an evaporating device at a rate of 305.7 kg per hour, and dehydrated. Then, 264 kg of the resulting mixture consisting of 83 kg of sodium β-naphthol and 181 kg of light oil was fed into mixer 1 (in FIG. 3) where β-naphthol was added at a rate of 57.2 kg per hour and mixed and dispersed. The dispersion was separated in separating tank 2. About two-thirds of the upper light oil layer was removed, and in the same way as in Example 7, sent to a recovery device. The liquid mixture consisting of 79.1 kg of sodium β-naphtholate, 27.5 kg of β-naphthol and 79 kg of light oil which remained in the separating tank 2 was fed into reactor 3 at a rate of 185.6 kg per hour, and reacted with carbon dioxide under a pressure of 3 kg/cm$^2$.G at a temperature of 270° C. with a residence time of 4.5 hours. The reaction mixture was worked up in the same way as in Example 8. Thus, 40.5 kg of 2-hydroxynaphthalene-3-carboxylic acid (melting range 220°–221° C.) was obtained per hour.

The yield of the product was 45.1% based on sodium β-naphtholate, and 86.6% based on the β-naphthol consumed. The amount of β-naphthol recovered was 60.3 kg per hour, and the ratio of recovery of β-naphthol was 92.6%.

What we claim is:

1. In a process for preparing 2-hydroxynaphthalenecarboxylic acid by the reaction of an alkali β-naphtholate with carbon dioxide, the improvement which comprises reacting a liquid mixture of the alkali β-naphtholate, 0.05 to 3 moles of β-naphthol per mole of the alkali β-naphtholate and 0.1 to 5 times the weight of the alkali β-naphtholate of light oil or kerosene with carbon dioxide under a carbon dioxide pressure of not more than 15 kg/cm$^2$.G at a temperature of at least 180° C.

2. The process of claim 1 wherein the liquid mixture is obtained by dehydrating the alkali β-naphtholate in the light oil or kerosene and then adding β-naphthol.

3. The process of claim 1 wherein the liquid mixture is obtained by dehydrating a mixture of the alkali β-naphtholate and β-naphthol in the light oil or kerosene.

4. The process of claim 1 wherein the liquid mixture is obtained by removing the excess of the light oil or kerosene by a liquid separating technique from a mixture consisting of alkali β-naphtolate, β-naphthol and light oil or kerosene.

5. The process of claim 1 wherein the liquid mixture is obtained by removing the excess of light oil or kerosene by a liquid separating technique from a mixture consisting of the alkali β-naphtholate, β-naphthol and light oil or kerosene, and then adding β-naphthol.

6. In a process for preparing 2-hydroxynaphthalenecarboxylic acids by the reaction of an alkali β-naphtholate with carbon dioxide, the improvement which comprises reacting a liquid mixture consisting of the alkali β-naphtholate, 0.05 to 3 moles of β-naphthol per mole of the alkali β-naphtholate and 0.1 to 5 times the weight of the alkali β-naphtholate of light oil or kerosene with carbon dioxide under a carbon dioxide pressure of not more than 15 kg/cm$^2$.G at a temperature of at least 180° C., adding water to the reaction mixture after the reaction, separating the light oil or kerosene layer before or after liberating the unreacted alkali β-naphtholate as β-naphthol by an acid, sedimenting and separating a tarry layer containing β-naphthol and resinous matter as a liquid from the aqueous layer, extracting the aqueous layer with a hydrophobic extracting solvent to separate β-naphthol, and then separating the desired product from the aqueous layer after the extraction by acid precipitation.

7. The process of claim 6 wherein an acid is further added to the aqueous layer from which the light oil or kerosene layer has been separated.

8. The process of claim 6 wherein β-naphthol is recovered from the light oil or kerosene layer and/or the tarry layer and/or the solvent extract layer either as such or as alkali β-naphtholate by reacting an alkali hydroxide.

9. In a process for preparing 2-hydroxy naphthalenecarboxylic acids, by the reaction of an alkali β-naphtholate with carbon dioxide, the improvement which comprises dehydrating the alkali β-naphtholate or a mixture of it with β-naphthol in light oil or kerosene to form a liquid mixture consisting of alkali β-naphtholate, 0.05 to 3 moles, per mole of alkali β-naphtholate of β-naphthol and 0.1 to 5 times the weight of the alkali β-naphtholate of light oil or kerosene, reacting the liquid mixture with carbon dioxide under a carbon dioxide pressure of not more than 15 kg/cm$^2$.G at a temperature of at least 180° C., adding water to the reaction mixture after the reaction, separating the light oil or kerosene layer before or after liberating the unreacted alkali β-naphtholate as β-naphthol by an acid, sedimenting and separating a tarry layer containing β naphthol and resinous matter as a liquid from the aqueous layer, further extracting the aqueous layer with a hydrophobic extracting solvent to separate β-naphthol, and then separating the desired product from the aqueous layer after the extraction by acid precipitation, wherein β-naphthol is recovered from the light oil or kerosene layer and/or the tarry layer and/or the solvent extract layer either as such or as alkali β-naphtholate by reacting an alkali hydroxide and recycled to the dehydration step or reaction step, and wherein the dehydration step, reaction step and the subsequent steps are carried out successively.

10. The process of claim 9 wherein an acid is further added to the aqueous layer from which the light oil or kerosene layer has been separated.

11. The process of claim 1 wherein the light oil of kerosene has a boiling point temperature in the range of 180°–350° C.

12. The process according to claim 1 which comprises reacting a liquid mixture of the alkali β-naphtholate, 0.2 to 2 moles of β-naphthol per mole of the alkali β-naphthoate and 0.2 to 4 times the weight of the alkali β-naphtholate of light oil or kerosene with carbon dioxide under a carbon dioxide pressure of from about 1 to about 10 kg/cm$^2$.G at a temperature of from about 250° to about 280° C.

13. The process according to claim 12 wherein the amount of the light oil or kerosene is from about 0.5 to about 3 times the weight of the alkali β-naphtholate and wherein said carbon dioxide pressure is from about 2 to about 7 kg/cm$^2$.G.

* * * * *

UNITED STATES PATENT AND TRADEMARK OFFICE
CERTIFICATE OF CORRECTION

PATENT NO. : 4,239,913
DATED : December 16, 1980
INVENTOR(S) : Ryuzo Ueno; Hiroaki Tsuchiya; Yasukazu Muramoto; Yoshihiko Kuwae.

It is certified that error appears in the above—identified patent and that said Letters Patent is hereby corrected as shown below:

Page 1, please change the name of the Assignee to read as follows:
    Kabushiki Kaisha Ueno Seiyaku Oyo Kenkyujo, Osaka, Japan Page 1, under References Cited, please change "4,002,673" to read ---4,002,675---.

Claim 1, line 2, please amend "acid" to read ---acids---.

Signed and Sealed this

Second Day of June 1981

[SEAL]

Attest:

RENE D. TEGTMEYER

Attesting Officer

Acting Commissioner of Patents and Trademarks